United States Patent [19]

Patrick et al.

[11] Patent Number: 4,707,356
[45] Date of Patent: Nov. 17, 1987

[54] SYNTHETIC PEPTIDE-BASED ANTI-RABIES COMPOSITIONS AND METHODS

[75] Inventors: James W. Patrick, Solana Beach; Stephen F. Heinemann, La Jolla; Barbara D. Boss, San Diego; W. Maxwell Cowan, Cardiff by the Sea, all of Calif.

[73] Assignee: The Salk Institute for Biological Studies, San Diego, Calif.

[21] Appl. No.: 941,163

[22] Filed: Dec. 12, 1986

Related U.S. Application Data

[62] Division of Ser. No. 752,222, Jul. 3, 1985, Pat. No. 4,652,629.

[51] Int. Cl.$^4$ ............................................ A61K 37/02
[52] U.S. Cl. ..................................................... 424/88
[58] Field of Search ........................................... 424/88

[56] References Cited

U.S. PATENT DOCUMENTS 4,195,265  4/1980  Koprowski et al. ................. 435/2
4,393,201  7/1983  Curtis et al. ......................... 536/27

FOREIGN PATENT DOCUMENTS 0117657  9/1984  European Pat. Off. .

OTHER PUBLICATIONS

Lentz et al., "Amino Acid Sequence Similarity Between Rabies Virus Glycoprotein and Snake Venom Curaremimetic Neurotoxins," Science 226, 847–848 (1984).
Immunization Practices Advisory Committee, "Rabies Prevention–United States 1984", Morbidity and Mortality Weekly Report 33, 393–402, 407–408 (1984).
Yelverton et al., "Rabies Virus Glycoprotein Analogs: Biosynthesis in *Escherichia coli,*" Science 219, 614–620 (1983).
Lentz et al., "Is the Acetylcholine Receptor a Rabies Virus Receptor?," Science 215, 182–184 (1982).
Anilionis et al. "Structure of the Glycoprotein Gene in Rabies Virus," Nature 294, 275–278 (1981).
Watson et al., "Entry of Rabies Virus into the Peripheral Nerves of Mice," J. Gen. Virol. 56, 371–382 (1981).
Flamand et al., "Use of Hybridoma Monoclonal Antibodies in the Detection of Antigenic Differences Between Rabies and Rabies–Related Virus Proteins, II, The Glycoprotein," J. Gen. Virol. 48, 105–109 (1980).
Karlsson, "Chemistry of Protein Toxins in Snake Venoms," Handbook Exp. Pharmacol. 52, 159–212 (1979).
Tsernoglou et al., "Structure and Function of Snake Venom Curarimimetic Neurotoxins," Mol. Pharmacol. 14, 710–716 (1978).
Dietzschold et al., "Structure and Function of Rabies Virus Glycoprotein", Develop. Biol. Standard 40, 45–55 (1978).
Ryden et al., "A Model of the Three-Dimensional Structure of Snake Venom Neurotoxins Based on Chemical Evidence," Int. J. Peptide Protein Res. 5, 261–273 (1973).
Dietzschold et al., "Antigenic Structure of Rabies Virus Glycoprotein: Ordering and Immunological Characterization of the Large CNBr Cleavage Fragments," J. Virology 44, 595–602 (1982).

*Primary Examiner*—Delbert R. Phillips
*Attorney, Agent, or Firm*—Fitch, Even, Tabin & Flannery

[57] ABSTRACT

A sequence in the coat glycoprotein of rabies virus is identified as the molecular basis for an essential step in the pathogenesis of the virus, the binding of virus to acetylcholine receptor at neuromuscular junctions prior to virus uptake into peripheral nerves. Based on this discovery, synthetic peptide-based, anti-rabies vaccines are prepared. The active ingredient of such vaccines is a synthetic protein, which is a conjugate with an immunogenic carrier protein of a synthetic peptide with a sequence which includes a sequence which is substantially the same as a substantial portion of the sequence of the acetylcholine receptor-binding segment of the rabies virus coat protein. Anti-rabies antisera, and anti-rabies antibodies, are prepared by injecting a mammal with a synthetic protein of the invention in a manner that induces an immune response in the mammal against the synthetic protein. Hybridomas which secrete anti-rabies antibodies, which bind to specific epitopes on or near the acetylcholine receptor binding segment on the rabies virus coat glycoprotein, are prepared with B cells immunized in vitro with a synthetic peptide or synthetic protein of the invention or taken from a mammal inoculated with such a peptide or protein. The anti-rabies vaccines of the invention avoid risks associated with currently available anti-rabies vaccines. The antisera and antibodies of the invention are useful therapeutically to induce passive anti-rabies immunity in a mammal that has been exposed to rabies virus. The antisera and antibodies are also useful for diagnosing whether a mammal is rabid and whether a mammal has been exposed to live rabies virus.

12 Claims, No Drawings

SYNTHETIC PEPTIDE-BASED ANTI-RABIES COMPOSITIONS AND METHODS

This is a division of application Ser. No. 752,222, filed July 3, 1985, now U.S. Pat. No. 4,652,629.

TECHNICAL FIELD

The present invention is directed to vaccines, antisera, and antibodies for the prevention and diagnosis of rabies. More particularly, it relates to synthetic peptide-based anti-rabies vaccines and antisera and antibodies generated by immunization with such vaccines.

BACKGROUND OF THE INVENTION

Rabies is a disease which affects humans and other mammals, including dogs and cattle.

Rabies is caused by a neurotrophic arbovirus of the rhabdovirus family, Lyssavirus genus.

The virus is transmitted from victim to victim in saliva. Once inoculated into a new host via a bite by a rabid animal, the virus concentrates at neuromuscular junctions, where it is taken up into nerve cells. Watson et al., J. Gen. Virol. 56, 371(1981); Lentz et al., Science 215, 182-184(1982). Once inside a nerve cell, the virus is transported in the retrograde direction along nerve processes and eventually reaches the spinal cord and brain. The virus replicates in and is released from spinal cord and brain cells. Upon release from nerve cells, the virus travels to the salivary glands, where it infects the acinar cells, from which virus is released into the saliva in very high numbers. The virus, at high titer in the saliva, can then be inoculated by a bite into another animal.

Most importantly, replication of the virus in the brain cells destroys the cells and produces an encephalitis, which may eventually kill the victim.

Blocking access of rabies virus to nerve cells of a mammal bitten by a rabid animal would block development of the disease in the former.

A person exposed to rabies virus, typically through an animal bite, is treated today in three ways. First, the bite wound is thoroughly washed with soap and water. Second, as soon as possible after the exposure, human antirabies gamma globulin, isolated from plasma of human donors hyperimmunized with inactivated rabies virus vaccine, is administered by intramuscular injection and is thoroughly infiltrated into tissue at and around the wound site. If human gamma globulin is not available, equine antirabies serum is used instead. The gamma globulin or serum formulation provides a passive anti-rabies immunity, because it contains antibodies which bind to rabies virus and facilitate virus removal from the bitten individual's system before the virus can establish itself by invasion of the person's nerve cells. The passive immunity conferred by the anti-rabies gamma globulin of anti-serum has a half-life of about 3 weeks. Third, in addition to the other steps, the person is vaccinated by intramuscular injection of five or six doses of inactivated rabies virus, the first vaccination being as soon as possible after the exposure and the others at 3, 7, 14, 28 and, optionally, 90 days after the first. Beginning 7 to 10 days after the first dose, the vaccine causes the person to mount an active immune response against the rabies virus; antibodies produced in this response mediate neutralization of the virus before it can become established in the exposed individual. See ACIP (Immunization Practices Advisory Committee) Recommendations on Rabies Prevention, Morbidity and Mortality Weekly Report 33, 393 (July 20, 1984) (Centers for Disease Control, Atlanta, Ga., U.S.A.).

As a prophylactic measure, persons subject to high risk of infection with rabies virus, via contact with rabid animals, work with rabies virus or otherwise, may be immunized against the virus with inactivated-virus vaccines. See ACIP (July 20, 1984), supra.

As a means of rabies control, domesticated mammals, such as dogs, cats, horses, and cattle, may be immunized against rabies virus by vaccination by injection with inactivated or attenuated virus or with the coat glycoprotein isolated from the virus. Oral vaccines, based on attenuated virus, have been developed and used in attempts to immunize populations of wild animals, such as foxes, against rabies.

There are a number of risks associated with the currently available, anti-rabies vaccines. The vaccines which contain inactivated or attenuated virus occasionally produce neurologic or central nervous system disorders in those vaccinated. Further, there is a risk that all of the virus in a lot of supposedly inactivated-virus vaccine will not be killed, or that some of the virus in a lot of attenuated-virus vaccine will revert to a virulent state, and that rabies might be caused in an individual mammal by vaccination with a dose which happens to contain live, virulent virus. A sythetic-peptide based anti-rabies vaccine would not involve these risks and would be substantially safer than the currently available vaccines.

Vaccines based on coat glycoprotein isolated from the virus entail many of the risks associated with inactivated- or attentuated-virus vaccines, because obtaining coat glycoprotein involves working with live virus.

Antisera, from which anti-rabies gamma globulin is derived for use in conferring passive immunity against the disease on persons who have been exposed to live virus, is taken from humans who have been hyperimmunized with inactivated rabies virus, as indicated above. Thus, obtaining anti-rabies gamma globulin is at least as risky as vaccination with currently available vaccines.

Obtaining antisera requires withdrawing blood, which also entails some risk. Further, administration of fractions from antisera entails a number of dangers similar to those associated with blood transfusion.

The risks associated with obtaining and using anti-rabies gamma globulin could be avoided by producing antibodies, effective to block establishment of rabies in individuals exposed to live rabies virus, in large quantity in substantially pure form, as by culturing hybridomas which secrete such antibodies. These risks would be reduced even further if production of the hybridomas was based on immunization of mammals, or in vitro immunization of mammalian lymphocytes, with synthetic, peptide-based, anti-rabies vaccines, which, as indicated supra, entail far less risk than vaccines based on inactivated or attenuated virus or proteins obtained from cultured virus.

Synthetic vaccines are known wherein an haptenic, synthetic peptide is linked to an immunogenic carrier molecule, which induces a mammal's immune system to produce antibodies against the haptenic peptide. The haptenic peptide in such vaccines has an amino acid sequence which includes a sequence which is the same as, or closely similar to, the sequence of an antigenic determinant on the toxin or infectious agent against which the vaccine is intended to provide protection. It has been found that some of the antibodies, raised in a mammal immunized with such a synthetic vaccine, will bind to the corresponding antigenic determinant on the surface of the toxin or infectious agent. Thus, such vaccines provide immune protection against intoxication or infection with toxin or infectious agent against which the vaccine is directed. The key to developing such a vaccine is identifying an antigenic determinant, on the toxin or infectious agent, which has a sequence of amino acids that is continuous, i.e., the determinant is an uninterrupted fragment of the primary structure of the protein on which the determinant occurs.

Typically, numerous strains of a virus will occur naturally. The various strains may be antigenically variable, i.e. differ from one another in the amino acid sequences of one or more of their antigenic determinants. Thus, a vaccine based on a single strain of a virus may not provide immunity in a vaccinated individual against other strains of the same virus, as antibodies induced by the single strain may not be reactive with antigenic determinants on other strains. Despite having been vaccinated, such an individual will remain susceptible to the disease caused by the virus. This problem of antigenic variability has in fact been encountered with currently available anti-rabies vaccines. Thus, in a synthetic vaccine, it is advantageous to use as the synthetic peptide one which includes an amino acid sequence identical, or closely similar, to that of an antigenic determinant on the target virus which cannot differ in sequence among strains of the virus. Such determinants will be those which are essential to propagation of the virus and which cannot fulfill their essential role in propagation if their sequences change. The sequences of such determinants will be highly conserved among all strains of a virus. Thus, a vaccine with a synthetic peptide with such a sequence will not be limited by antigenic variability and will be effective to provide protection against all strains of the virus against which the vaccine is intended to provide protection. Of course, making such a vaccine requires identifying an antigenic determinant on the virus which has a sequence that is highly conserved among the various strains.

Lentz et al., supra, have shown that the rabies virus particle attaches to muscle cells in culture and that the distribution of virus parallels the distribution of acetylcholine receptor. Further, Lentz et al. have reported data which indicate that rabies virus accumulates at the neuromuscular junction by binding to the acetylcholine receptors (AChR's) at such junction. Among the findings reported by Lentz et al. is that binding of rabies virus at the neuromuscular junction can be blocked by pre-incubation of tissue including such junctions with the curaremimetic, snake-venom neurotoxin, alpha-bungarotoxin, which is known to bind tightly to the acetylcholine (ACh) binding site of the AChR.

The rabies virus particle is bullet-shaped. Its negative-strand RNA genome is enveloped by an outer protein covering from which numerous "spikes" protrude which are molecules of the rabies virus coat glycoprotein (G protein). This glycoprotein is responsible for the immunogenicity of the virus. Thus, antigenic determinants of the virus are on the G protein.

Monoclonal antibodies have been prepared using various strains of whole rabies virus. Flamand et al., J. Gen. Virol. 48, 105(1980).

Antibodies raised against the coat glycoprotein can neutralize infectious virus. See Dietzschold et al., Dev. Biol. Stand. 40, 45(1978).

The sequences of the coat glycoproteins from two strains of rabies virus are known. Anilionis et al., Nature 294, 275-278(1981); Yelverton et al., Science 219, 614-620(1983). These glycoproteins, in mature form, as they occur in the coat, of the virus outside infected cells, have sequences of 505 amino acids. The sequences are approximately 90% homologous.

Numerous curaremimetic, snake-venom neurotoxins, similar to alpha-bungarotoxin, are known which bind with high affinity at the ACh binding site of the AChR at neuromuscular junctions. The sequences of more than 60 of these neurotoxins are known. Studies of these neurotoxins, involving three-dimensional structural determinations, chemical modifications, and comparisons of sequences, have led to identification of four highly conserved amino acids which interact to form and stabilize a structure, which is similar to that of ACh and is thought to be involved in the binding of the neurotoxins to the active-site (i.e., the ACh binding-site) of the AChR. According to the amino acid numbering system based on the alignment of neurotoxin sequences by Karlsson (Handbook of Experimental Pharmacology 52, 159-212(1979), these four residues are tryptophan at position 29, aspartate at position 31, arginine at position 37 and glycine at position 38. The tryptophan at position 29 is thought to stabilize an ion-pair formed between the carboxylate group of aspartate-31 and the guanidinium group of arginine-37. It is this ion-pair which is thought to stereochemically mimic acetylcholine (Tsernoglou et al., Mol. Pharmacol. 14, 710(1978)). Modification of the tryptophan-29 results in a loss of toxic activity of no more than about 50% (Ryden et al., Int'l. Jour. Peptide Protein Res. 5, 261-273(1973)).

SUMMARY OF THE INVENTION

We have discovered that a segment of the rabies virus coat glycoprotein has a sequence which is homologous with the conserved sequences of the segment of the curaremimetic, snake-venom neurotoxins which includes the segment through which the toxins are thought to bind to the ACh binding-site of the AChR at neuromuscular junctions.

Our discovery is illustrated in Table I, where sequences from corresponding segments of the two rabies virus coat glycoproteins whose sequences are known are compared with sequences of the segments of several curaremimetic snake-venom neurotoxins through which the toxins are thought to bind in the ACh binding site of the AChR. Aspartate-190, arginine-196, and glycine-197 in the coat protein sequences correspond to the aspartate-31, arginine-37 and glycine-38 (following the numbering system of Karlsson), respectively, in the toxin sequences. The high degree of homology between the sequences of the illustrated segments of the two coat proteins is also apparent in the Table.

TABLE I

| COMPARISON OF AMINO ACID SEQUENCES OF RABIES VIRUS COAT GLYCOPROTEINS AND CURAREMIMETIC SNAKE-VENOM NEUROTOXINS | | |
|---|---|---|
| PROTEIN | SEQUENCE* | REFERENCE |
| Rabies Virus (ERA strain) coat glycoprotein | (183) PLGMSCDIFTNSRGKRASKG-SET | 1 |
| Rabies Virus (CVS strain) coat glycoprotein | (183) PRPGTPCDIFTNSRGKRASNG-NKT | 2 |

TABLE I-continued
COMPARISON OF AMINO ACID SEQUENCES OF RABIES VIRUS COAT GLYCOPROTEINS AND CURAREMIMETIC SNAKE-VENOM NEUROTOXINS

| PROTEIN | SEQUENCE* | REFERENCE |
|---|---|---|
| Long Neurotoxins: | | |
| B: multicinctus alpha-bungarotoxin | (23) CYRKMWCDAFCSSRGKVVELGCAAT | 3 |
| N. naja oxiana toxin I | (22) CYTKTWCDAWCGSRGKVIELGCAAT | 3 |
| O. hanna toxin a | (21) CYTETWCDAWCTSRGKRVDLGCAAT | 3 |
| N. melanoleuca toxin b | (20) CYTKTWCDNFCASRGKRVDLGCAAT | 3 |
| N. naja siamensis toxin 3 | (20) CYTKTWCDAFCSIRGKRVDLGCAAT | 3 |
| D. viridis toxin 4, 7, 3 | (21) CYTETWCDAWCSQRGKREELGCAAT | 3 |
| Short Neurotoxins: | | |
| N. nivea toxin beta | (23) CYKKRWRD-H — RGTIIERGC — G | 3 |
| N. naja atra cobratoxin | (24) CYKKRWRD-H — RGYRTERGC — G | 3 |
| H. haemachatus toxin IV | (23) CYKKQWSD-H — RGSRTERGC — G | 3 |

*The position in the mature protein of the N-terminal residue of the sequence shown is indicated in parentheses before the sequence.
1 Anilionis et al., nature 294, 275(1981)
2 Yelverton et al., Science 219, 614(1983)
3 Karlsson, Handb. Exp. Pharmacol. 52, 159(1979)

Our discovery suggested that the segment of the coat glycoproteins that is homologous with the AChR binding segments of the neurotoxins is involved in the binding of rabies virus to the AChR. This suggestion was strengthened by our finding that a three-dimensional model of this segment of the virus glycoproteins fits snugly in a three-dimensional model of the ACh binding site of the AChR.

The suggestion indicated, further, that this segment of the glycoproteins would be exposed and accessible to antibodies and, thus, be an antigenic determinant of rabies virus. Further, the segment would likely be highly conserved in the various strains of the virus because of the apparently essential role of AChR-binding in the pathogenesis of rabies. Thus, our discovery suggested to us that synthetic peptides, with sequences closely similar to the sequences of the segments on the coat proteins homologous to the sequences of the AChR-binding segments of the curaremimetic snake-venom neurotoxins, could be used as the basis for making synthetic vaccines against rabies, caused by virtually any strain of the virus.

We have found that in fact synthetic peptides with sequences which include a sequence closely similar to CDIFTNSRG, when conjugated to a suitable immunogenic carrier protein and, as part of such conjugates, inoculated into mammals, do protect the mammals from rabies when they are challenged with live rabies virus.

We have thus discovered synthetic peptides which are the basis for synthetic, anti-rabies vaccines.

The synthetic peptides of the invention also provide the basis for preparing novel anti-rabies antisera, and anti-rabies antibodies, both polyclonal and monoclonal. Such antisera and antibodies are useful in diagnosing and preventing rabies.

DETAILED DESCRIPTION OF THE INVENTION

We have discovered the molecular basis for the binding of rabies virus to the AChR that precedes viral uptake into nerve termini at neuromuscular junctions. In particular, we have found that the virus binds to the ACh binding-site of the AChR through a segment of its coat glycoprotein which has a sequence homologous to the conserved sequence of segments of certain curaremimetic, snake-venom neurotoxins which also bind to the ACh binding-site of the AChR.

This finding is supported by the close fit we have found in three-dimensional modeling of this segment of the rabies virus coat glycoprotein and the ACh binding-site of the AChR. (With regard to the ACh binding-site, see Luyten, W. H. M. L., Kellaris, K., Kyte, J., Heineman, S. and Patrick, J., "A Model for the ACh Binding Site of the AChR." Society of Neurosciences Abstracts, No. 212.10(1984)).

As noted, supra, an essential step in the pathogenesis of rabies virus is its accumulation at the neuromuscular junction, which is mediated by its binding to the AChR. Consistent with the central role of AChR-binding in viral propagation, the segment of the coat glycoprotein responsible for the binding is highly conserved in the two strains of the virus for which coat glycoprotein sequences are known. See Table I.

From the homology between the two, known rabies virus coat glycoprotein sequences over the segment indicated, by modelling as well as comparison with conserved, AChR-binding segments of the curaremimetic snake-venom neurotoxins, it is clear that the sequence

CDIFTNSRG is the sequence of the segment of the rabies virus coat glycoprotein which fits closely into the ACh binding-site of the AChR. Further, it appears that, in this sequence, the D, R, G, and possibly the C are essential. The segment would still function to bind the glycoprotein and virus at the ACh binding-site if the I residue were replaced with G or an amino acid with an alkyl side chain, if the F were replaced with W, if the T were replaced with C or S, if the N were replaced with S, T, A, or G, and if the S were replaced with a T, a G, or an amino acid with an alkyl side chain.

From the fact that the segment of the rabies virus coat protein, through which the virus binds to the ACh binding-site, must protrude from the viral surface to effect the connection to the binding-site, it was apparent that the segment or a portion thereof would likely be an antigenic determinant of rabies virus.

In fact, we have found that a synthetic peptide which includes the sequence

CDIFTX$_6$SRG, wherein X$_6$ is N or T, when conjugated to a carrier protein that is immunogenic in a mammal, and, as part of such a conjugate, inoculated into said mammal, will protect the mammal against challenge with live rabies virus, by causing the production in the mammal of antisera which includes antibodies that neutralize rabies virus. Thus, we have discovered a novel class of synthetic peptide-based, anti-rabies vaccines.

Further, we have discovered novel anti-rabies antisera, and antibodies, and novel hybridomas which secrete such antibodies, all of which are readily prepared by the skilled using the novel vaccines of the invention, the synthetic proteins of the invention, which are the essential immunogenic component of the vaccines, or the synthetic peptides of the invention which are the essential component of the synthetic proteins.

Further, our discovery provides methods for immunizing mammals against rabies, with vaccines, antisera and antibodies of the invention, as well as methods for producing the antisera, antibodies and hybridoma cultures of the invention.

Our discovery also provides methods, using the synthetic peptides and synthetic proteins of the invention, for assaying the serum of a mammal that has been vaccinated against rabies for the presence of anti-rabies antibody.

Still further, the antisera and antibodies that can be produced by our invention provide methods of testing, for the presence of rabies virus, tissue or saliva from mammals suspected of being rabid, or of having been put at risk of contracting rabies by exposure to rabies virus via a bite from a rabid animal or otherwise.

Abbreviations for amino acids used in the present specification are listed in the following Table II:

TABLE II

| AMINO ACID | ABBREVIATION | LETTER-ABBREVIATION |
|---|---|---|
| Alanine | Ala | A |
| Arginine | Arg | R |
| Asparagine | Asn | N |
| Aspartic Acid | Asp | D |
| Cystine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

All amino acids referred to in the present specification which have optical isomers are of the L configuration.

Sequences of peptides are written with the N-terminal amino acid at the beginning, reading from left to right.

Rabies virus "coat protein," rabies virus "glycoprotein," rabies virus "coat glycoprotein", and rabies virus "G protein" are used interchangeably in the present specification to refer to the antigenic glycoprotein, of about 505 amino acids in "mature form", which forms the surface spikes of enveloped rabies virus.

In the present specification, "ACh" means "acetylcholine" and "AChR" means "acetylcholine receptor."

Reference herein to the term "mammal" includes both human and non-human mammals.

In the present specification, a mammal is said to be "rabid" if it has rabies virus in its saliva that are being released from the rabies virus-infected acinar cells of its salivary glands.

Reference herein to a mammal that has been "exposed to rabies virus" means a mammal that has been in contact with the virus in a way that puts the mammal at a high risk of contracting rabies. The most common form of such exposure is by a bite from a rabid animal. Other forms of such exposure include contacting a scratch, abrasion, open wound or mucous membrane with saliva or other potentially infectious material (e.g. brain tissue) from a rabid animal or some other source of live virus (as in a laboratory culture). See, e.g., ACIP(1984), supra.

In the instant specification, the terms "anti-rabies vaccine" and "composition for vaccinating a mammal against rabies" are used interchangeably.

In one of its aspects, the present invention includes a synthetic peptide which has an amino acid sequence comprising the sequence $CDIFTX_6SRG$, wherein $X_6$ is N or T, said peptide, when conjugated to a carrier protein which is immunogenic in a mammal, being capable of raising in the mammal an immune response against rabies virus.

Those of skill in the art will understand that the flexibility, when conjugated to carrier protein, of the segment of the synthetic peptide with sequence $CDIFTX_6SRG$ is essential to its ability to induce an immune response against rabies virus, based on the similarity of all or part of the segment to an antigenic determinant of the virus, as discussed supra. Thus, to preserve flexibility of the $CDIFTX_6SRG$ segment, the synthetic peptide preferably will have a terminal amino acid, such as a Y, which does not otherwise occur in the peptide's sequence and through which the peptide can be conjugated to the carrier protein.

Preferred anti-rabies virus antigenic synthetic peptides of the invention have a sequence of $(Y)_iX_{-1}$-$CDIFTX_6SRGKRASX_{14}G(Y)_j$, wherein one of i and j is 0 and the other is 1 and wherein $X_{-1}$ is S or P, $X_6$ is N or T, and $A_{14}$ is N or K. Most preferred among these peptides is that with the sequence SCDIFTTSRG-KRASKGY.

The invention also includes certain other peptides which, like those recited in the preceding paragraph, are useful per se in screening for hybridoma cultures which include hybrid cells which secrete antibody of the invention and for testing the serum of a mammal that has been vaccinated against rabies for the presence of anti-rabies antibody. Among these peptides are those with the sequences $CDIFTX_6SRG$ and $X_{-1}CDIF$-$TA_6SRGKRASA_{14}G$, wherein $X_{-1}$ is S or P, $X_6$ is N or T, and $X_{14}$ is N or K.

The peptides of the invention can also be employed directly, without conjugation to a carrier protein, to inoculate a mammal in vivo or B cells from a mammal in vitro to generate B cells for preparation of hybridomas of the invention.

Also within the scope of the invention are radioactively labeled peptides with sequences of peptides of the invention, including those wherein one or more tyrosines are labeled with $^{125}I$, those wherein one or more of carbons are replaced with $^{14}C$, those wherein one or more hydrogens are replaced with $^3H$, and those wherein one or more sulfurs are replaced with $^{35}S$. The radioactively labeled peptides are useful in purifying synthetic peptides of the invention, screening for hybridomas of the invention, and diagnosing the presence of anti-rabies antibody in mammalian serum.

In another of its aspects, the invention includes synthetic proteins which comprise a synthetic, anti-rabies antigenic peptide of the invention conjugated to a carrier protein which is immunogenic in a mammal, said synthetic protein being capable of raising in said mammal an immune response against rabies virus.

Numerous suitable carrier proteins are known in the immunological arts, and any of these may be used as a part of the synthetic protein of the invention. Among the carrier proteins are ovalbumin, serum albumin from any mammalian species, globulins such as beta-lactoglobulin, oxygen-transporting proteins such as hemoglobins, or subunits thereof, myoglobins, hemocyanins and the like, and any of the various synthetic polypeptides which have been utilized as immunogenic carriers for small, haptenic molecules. The function of the carrier protein in a mammal immunized with it is stimulation of the mammal's immune system, presumably through activation of T-helper cells, to produce antibody, including antibody against the synthetic peptide conjugated to the carrier. In this regard, it is preferred to use, with a mammal of a given species, a carrier protein from a mammal of a different species. The preferred carrier proteins for use in the synthetic proteins of the invention are bovine serum albumin (BSA) and keyhole limpet hemocyanin (KLH). If the species to be immunized with the synthetic protein is of the genus Bos, the preferred carrier protein is KLH.

Any of the means of conjugating a synthetic-peptide hapten to an immunogenic carrier protein may be used to make the synthetic proteins of the invention. However, for the reasons indicated supra relating to preservation of the integrity and flexibility of at least the sequence CDIFTX$_6$SRG of the synthetic peptide conjugated to the carrier protein, it is preferred that the conjugation be through a tyrosine residue at one terminus of the synthetic peptide. The preferred method for effecting this conjugation is with bis-diazotized benzidine (BDB).

The preferred synthetic proteins of the invention are those wherein the synthetic peptide has an amino acid sequence of $(Y)_iX_{-1}CDIFTX_6SRGKRASX_{14}G(Y)_j$, wherein one of i and j is 0 and the other is 1 and wherein $X_{-1}$ is S or P, $X_6$ is N or T, and $X_{14}$ is N or K and said synthetic peptide is conjugated through its tyrosine residue with BDB to BSA or KLH. Most preferred among these synthetic proteins are those wherein the amino acid sequence of the synthetic peptide is SCDIFTTSRGKRASKGY, provided that, when the synthetic protein is to be used to immunize a mammal of genus Bos, the preferred carrier protein will be KLH.

The synthetic proteins of the invention are the essential ingredient in the vaccines of the invention in that the synthetic protein occasions in a vaccinated mammal an immune response against rabies virus. Thus, in another of its aspects, the invention involves vaccines for immunizing mammals against rabies which comprise a synthetic protein of the invention.

The compositions of the invention for immunizing mammals against rabies will include typically other components known to those skilled in the vaccine art. Among these components will be a diluent and an adjuvant that are pharmacologically acceptable for the mammal being vaccinated. The adjuvant promotes stimulation of the mammal's immune system to mount an effective immune response against the haptenic synthetic peptide conjugated to the carrier protein. An example of a physiologically acceptable diluent is physiological saline, such as phosphate-buffered saline (PBS). Examples of acceptable adjuvants include complete Freund's adjuvant, incomplete Freund's adjuvant, aluminum oxide, alum, and the like.

The preferred vaccines of the invention are those wherein the synthetic proteins are the preferred synthetic proteins of the invention. Thus, in the most preferred composition for vaccinating a mammal against rabies, the synthetic protein will be that wherein the synthetic peptide has the amino acid sequence SCDIFTTSRGKRASKGY, the carrier protein will be BSA or KLH, and the synthetic peptide will be conjugated to the carrier protein through the tyrosine residue with a BDB bridge. As with the synthetic proteins, if the mammal to be vaccinated is of the genus Bos, the most preferred vaccine will utilize KLH as the immunogenic carrier protein.

The vaccines of the invention can be employed prophylactically by immunization of a mammal prior to its exposure to rabies virus. The vaccines of the invention may also be used to treat mammals after they have been exposed to the virus. The vaccines induce an active anti-rabies immune response in inoculated mammals and, thereby, reduce the risk that the mammals will suffer rabies virus-induced encephalitis or become rabid.

The invention also contemplates a method of immunizing a mammal against rabies which comprises administering to said mammal an immunogenic amount of a vaccine of the invention. Immunization can be by administration of a single dose of vaccine. However, more typically, it will involve administration of a number of doses, typically at least two. Each dose will have an immunogenic amount of vaccine.

In prophylactic, pre-exposure immunization of humans, typically three doses, on days 0, 7, and 28, will be administered, by intramuscular injection. For persons at high risk of exposure to rabies virus, serum is tested at intervals ranging from about 6 months to about 2 years after the initial series of immunizations; if anti-rabies antibody titer is low, a booster dose is administered. Post-exposure immunization is required, and post-exposure administration of anti-rabies antibody is preferred, for persons immunized prior to exposure.

In treating a mammal that has been exposed to rabies virus, the method of immunization will involve a series of between about three and eight doses, typically over a period of about a month, and spaced at increasing intervals over that period, with additional doses two to four months after the initial series. The purpose of the dosage regime is to induce a massive, active immune assault against rabies virus that has been introduced into the mammal's system. Those of skill in the vaccine art will understand how to determine a dosage regimen that is appropriate for mammals of a particular species and, given a particular species, of particular age, weight, and medical condition. A post-exposure dosage regimen for humans is outlined supra, in the Background section.

In the course of administering to a mammal anti-rabies vaccine of the invention, the mammal's serum can be tested for the presence of anti-rabies virus antibody by any of numerous immunoassay methods well known in the art. Synthetic peptides and synthetic proteins of the invention are useful in certain of these methods. The presence of such antibody indicates that an active immune response to the virus has been mounted by the mammal and, if the titer of such antibody is sufficiently high, subsequent doses of vaccine will be contraindicated in certain circumstances. See ACIP (July 20, 1984), supra.

Administration to a mammal of an anti-rabies vaccine of the invention gives rise to an anti-rabies immune response in said mammal. This immune response entails the production of anti-rabies antibody. Thus, a vaccinated mammal which has mounted an immune response against rabies virus will have serum which contains anti-rabies antibodies. Clearly, then, another aspect of the present invention is an antiserum made by a method which comprises inoculating a mammal with an immunogenic amount of a vaccine of the invention.

The preferred anti-rabies antisera of the invention are those prepared using the preferred vaccines of the invention. As indicated supra, antisera themselves or antibody fractions isolated from said antisera can be used to confer temporary, passive immunity against rabies virus on a mammal exposed to the virus and, thereby, prevent the development of rabies in said mammal. The most preferred antiserum for use directly, or to obtain antibody, for use in such treatments is an antiserum obtained from a mammal of the same species as the mammal to be treated.

Anti-rabies antibodies can be isolated from the anti-rabies antisera of the invention by any of a number of purification techniques well known in the protein chemistry and immunological arts. Typically, such purification will involve chromatographic procedures, such as high performance liquid chromatography or immunoaffinity chromatography.

The purification can include cold ethanol precipitation of gamma globulin fraction from plasma of a mammal hyperimmunized with a vaccine of the invention, the procedure currently employed to isolate anti-rabies gamma globulin from human volunteers hyperimmunized with inactivated rabies virus. See ACIP (July 20, 1984), supra.

An anti-rabies antibody of the invention is an antibody which is capable of binding to an epitope on a synthetic peptide of the invention or a synthetic protein of the invention and is capable of binding to rabies virus or rabies virus coat protein. Assays for these binding capabilities are described below.

Compositions comprising one or more of these antibodies of the invention, and typically also including pharmaceutically acceptable diluents such as PBS, can be used in essentially the same manner as an immunoglobulin fraction, isolated from an anti-rabies antiserum of the invention, to treat a mammal that has been exposed to rabies virus. The compositions comprising one or more of the antibodies of the invention, substantially free of other antibodies and other constituents of anti-rabies antiserum of the invention, are preferred, over whole antiserum or immunoglobulin fraction isolated therefrom, for treating mammals exposed to live virus in that the risk of side effects from the use of purified antibody is substantially less than with the use of the whole antiserum or the immunoglobulin fractions thereof.

The anti-rabies antisera of the invention, as well as the compositions of the invention comprising purified anti-rabies antibody, can also be used diagnostically, in any of a number of well known immunoassay techniques, to determine whether an animal is rabid or to determine whether a mammal suspected of having been exposed to rabies virus has in fact been exposed. In determining whether an animal is rabid, the saliva derived from said mammal can be tested for rabies virus using one of these immunological techniques. In determining whether a mammal has been exposed to the virus, a sample of fluid or tissue from the area of exposure similarly can be tested immunologically for the presence of rabies virus.

A mammal which has been vaccinated with a vaccine of the invention and, as a consequence, has mounted an immune response against rabies virus, will have B cells which secrete anti-rabies antibody of the invention.

As indicated above, a mammal inoculated with synthetic peptide of the invention that is not conjugated to a carrier protein will also have B cells which secrete anti-rabies antibody of the invention. Further, such B cells can be isolated from a suspension of B cells that have been isolated from a mammal and then in vitro immunized, particularly in the presence of an adjuvant peptide such as N-acetylmuramyl-L-alanyl-D-isoglutamine, with a synthetic protein or synthetic peptide of the invention. Thus, yet another aspect of the invention is an hybridoma culture which (i) is prepared by a process comprising forming hybridomas with B cells which secrete antibody of the invention and (ii) comprises hybrid cells which secrete an antibody of the invention. Any of the numerous techniques known in the art for forming hybridomas can be employed. The preferred hybridoma cultures of the invention are those which secrete an antibody of the invention which is capable of binding to an epitope on a peptide with a sequence $X_{-1}CDIFTX_6SRGKRASX_{14}G$, wherein $X_{-1}$ is S or P, $X_6$ is N or T, and $X_{14}$ is N or K. Most preferred are the hybridoma cultures which secrete an antibody of the invention capable of binding to a peptide with the sequence $CDIFTX_6SRG$, where $X_6$ is N or T.

Monoclonal antibodies produced by monoclonal, antibody-producing hybridoma cultures of the invention are especially advantageously applied, like antibodies of the invention isolated by physico-chemical techniques from antiserum of the invention, in treating mammals that have been exposed to rabies virus and in diagnosis of rabies, as discussed supra.

The peptides of the invention are synthetic, i.e. they are not found in nature. They are synthesized by any suitable method, such as by exclusively solid-phase techniques, partial solid-phase techniques, fragment condensation or classical solution addition.

The peptides can also be synthesized by recombinant DNA techniques.

The preferred peptides of the invention have fewer than about 25 amino acids and are preferably prepared chemically, i.e., not microbiologically on the basis of recombinant DNA technology.

Nonetheless, microbiological production, based on recombinant DNA techniques, may advantageously be employed to make larger peptides of the invention, particularly those with more than about 40 amino acids. Recombinant DNA techniques for making synthetic peptides in bacteria, such as E. coli and B. subtilis; yeast, such as S. cerevisiae and mammalian cells, and methods for isolating the desired peptide from cultures of such organisms transformed to make the peptide, are well known. See, e.g. Methods in Enzymology, vols. 68, 100 and 101 (Academic Press).

When a peptide of the invention is prepared chemically, it can be prepared by any of the numerous manual and automated methods known in the art. It can be prepared using solid-phase syntheses such as that described by Merrifield, J. Am. Chem. Soc. 85, 2149(1964), although other equivalent chemical syntheses known in the art can also be used. See Stewart and Young, Solid Phase Peptide Synthesis, W. H. Freeman Publishing Company, San Francisco, Calif.(1969). The synthesis can be carried out manually. Alternatively, it can be carried out on an automated peptide synthesizer, such as a Beckmann 990 Automatic Synthesizer (Beckmann Instruments, Palo Alto, CA, U.S.A.), programmed to make a peptide of desired sequence.

Solid-phase synthesis is commenced from the C-terminal end of the peptide by coupling a protected amino acid to a suitable resin; as generally set forth in Rivier et al., U.S. Pat. No. 4,244,946, the disclosure of which is incorporated herein by reference. If, for example, the carboxy-terminal amino acid is tyrosine, it can have its amino group protected by t-butyloxycarbonyl (BOC) and its phenolic hydroxy group protected by 2, 6-dichlorobenzyl (DCB) or p-bromobenzyloxycarbonyl (4-Br-Z) prior to coupling to a polystyrene resin.

A preferred resin for the synthesis is a chloromethylated polystyrene resin; such as may be obtained from BioRad Laboratories, Inc., Richmond, Calif. U. S. A.

The coupling of the protected, carboxy-terminal amino acid to the resin follows the procedure set forth in Horiki et al., Chemistry Letters 165–168 (1978), using potassium fluoride in dimethylformamide (DMF) at about 60° C. for 24 hours with stirring. Following coupling of the carboxy-terminal residue to the resin support, the alpha-amino protecting group is removed as by using triflouroacetic acid (TFA) in methylene chloride, TFA alone, or HCl in dioxane. Preferably 50 wt. % TFA in methylene chloride is used with 0 to 5 wt. % 1,2-ethanedithiol. The deprotection is carried out at a temperature between about 0° C. and room temperature (20° C. to 30° C.). Other standard cleaving reagents and conditions for removal of specific alpha-amino protecting groups may be used, as described by Schroder and Lubke, in The Peptides, Volume I, pages 72–75 (Academic Press, 1965).

After removal of the alpha-amino protecting group on the carboxy-terminal amino acid bound to the support, the next desired amino acid, protected at the alpha-amino group and any reactive side-chain functional group, is coupled to the amino group of the carboxy-terminal amino acid, and after its coupling, its alpha-amino protecting group is removed. This coupling-alpha-amino-protecting-group-removal procedure is followed with the remaining protected amino acids, in the order from carboxy- to amino-terminus dictated by the desired sequence of the final synthetic peptide, to obtain an intermediate peptide. This intermediate peptide has the same sequence as the desired synthetic peptide of the invention except that the reactive functional groups on the side chains of the amino acids are protected, as described infra, and the peptide remains bound to the resin.

As an alternative to adding each amino acid separately, some of them may be coupled to one another in a peptide segment prior to addition to the resin-bound carboxy-terminal end of the desired peptide.

Each protected amino acid or peptide segment is introduced into the solid phase reactor in about a fourfold excess and the coupling is carried out in a medium of DMF:$CH_2Cl_2$(1:1 by volume) or DMF or $CH_2Cl_2$ alone. This coupling is preferably carried out using as the coupling reagent dicyclohexylcarbodiimide (DCC), in the same molar concentration as amino acid or peptide segment to be coupled to the solid-phase-bound fragment. In instances where the coupling is carried out manually, the success of the coupling reaction at each stage of the synthesis is monitored by the ninhydrin reaction, as described by Kaiser et al., Anal. Biochem. 34, 595(1970). In cases where incomplete coupling occurs, the coupling procedure is repeated before removal of the alpha-amino protecting group prior to the coupling of the next amino acid. The coupling reactions can be performed automatically, as on a Beckman 990 Automatic Synthesizer, using a program such as that reported in Rivier et al. Biopolymers 17, 1927–1938(1978).

After the synthesis of the intermediate peptide (i.e. with reactive side-chain functional groups and, optionally, the N-terminal alpha-amino group protected) with the amino acid sequence of the desired final peptide has been completed, the intermediate peptide is removed from the resin support by treatment with a reagent, such as anhydrous HF, which not only cleaves the peptide from the resin at the anchoring bound but also cleaves the protecting group from the N-terminal alpha-amino group, if this protecting group has not already been removed, and all of the side-chain protecting groups. This procedure leaves the carboxyl group of the desired peptide with the carboxy-terminus in its free acid form.

Following is a list of protecting groups suitable for the peptide synthesis procedures described above:

The alpha-amino protecting groups are those known to be useful in the art in the step-wise synthesis of polypeptides. Among the classes of alpha-amino protecting groups which may be used are: (1) aromatic urethan-type protecting groups, such as fluorenylmethyloxycarbonyl(FMOC), benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (2) aliphatic urethan-type protecting groups, such as BOC, diisopropylmethoxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred alpha-amino protecting group is BOC.

A protecting group for the sulfhydryl group of C is benzyl(Bzl), substituted Bzl, e.g., 3,4-dimethyl benzyl, p-methoxybenzyl(MeOBzl), p-chlorobenzyl and p-nitrobenzyl, trityl, Z, substituted Z, thioethyl, or benzoyl (Bz). MeOBzl is preferred.

A protecting group for the amido group of N or Q is preferably xanthyl(Xan).

A protecting group for the hydroxyl group of T and S is preferably selected from the class consisting of acetyl(Ac), Bz, tert-butyl, trityl, tetrahydropyranyl, Bzl and DCB. Most preferred is Bzl. While preferred, it is not necessary, for obtaining acceptable yields, to protect the hydroxy group of T and S.

A protecting group for the phenolic hydroxyl group of Y is selected from the group consisting of tetrahydropyranyl, tert-butyl, trityl, Bz, Z, 4-Br-Z and DCB.

A protecting group for the guanidinium group of R is preferably selected from the class consisting of nitro, p-toluenesulfonyl(Tos), Z, adamantyloxycarbonyl and BOC. Tos is most preferred.

A protecting group for the imidazolium group of H is Tos, Bzl, trityl, 2,2,2-trifluoro-1-benzyloxycarbonylaminoethyl, 2,2,2-trifluoro-1-benzyloxycarbonylaminoethyl, and 2,4-dinitrothiophenyl.

Suitable protecting groups for the epsilon-amino group of K are Z, 2-chloro-Z, Tos, t-amyloxycarbonyl(Aoc), BOC and aromatic or aliphatic urethan-type protecting groups as specified above for protecting alpha-amino groups. The selection of a side-chain amino protecting group is not critical except that it should be one which is not removed during deprotection of the alpha-amino groups during the synthesis. Hence, the alpha-amino protecting group and the side chain epsilon-amino protecting group cannot be the same.

The beta-carboxyl group of D or the gamma-carboxyl of E is protected by forming an ester with a group, preferably selected from the class consisting of Bzl, DCB, methyl, ethyl and t-butyl. The Bzl ester is most preferred.

The remaining amino acids, A,F,G,I,L,M,P,V and W have side-chains that are sufficiently unreactive that they do not require protection.

In selecting a particular side-chain protecting group to be used in the synthesis of the peptide, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side-chain protecting group must be removeable, upon the completion of the synthesis of the peptide with the desired amino acid sequence, under reaction conditions that will not alter the peptide chain.

From the foregoing, it is apparent that the invention provides a method for manufacturing a synthetic peptide of the invention by, first, making an intermediate peptide with the amino acid sequence of the desired peptide of the invention that is either anchored to the solid-support on which it was synthesized or has the alpha-carboxy group on its C-terminal amino acid esterified, and, second, splitting off the protective group or groups and removing the peptide from the resin support or removing the ester group from the alpha-caboxy group of the C-terminal amino acid, and, third, if desired, converting the resulting synthetic peptide of the invention into a salt thereof.

Once cleaved from the resin, the peptides of the invention can be purified over a column of Sephadex G-25, by C-18 reverse-phase high performance liquid chromatography or by any other suitable, preferably chromatographic, technique, using standard procedures.

In certain applications, it may be desirable to have a peptide of the invention radiolabeled. A peptide of the invention which includes one or more tyrosine residues can be radiolabeled, before or after the peptide is purified chromatographically, with $^{125}I$ on the tyrosine group, by use, according to the manufacturer's instructions, of Enzymobeads ™ and Enzymobead Radioiodination Reagent, both available from Bio Rad Laboratories, Inc., Richmond, Calif., U.S.A. The chloramine T method of iodinating tyrosines can also be employed.

A peptide labeled with $^3H$, $^{14}C$ or $^{35}S$ can be prepared by using one or more amino acids so labeled in synthesis of the peptide.

We have found that with shorter peptides of the invention, such as the preferred peptides with a sequence of $$(Y)_i X_{31}|CDIFTX_6SRGKRASX_{14}G(Y)_j,$$

wherein one of i and j is 0 and the other is 1 and wherein $X_{-1}$ is S or P, and $X_6$ is N or T, and $X_{14}$ is N or K; that the peptides wherein the amino acid at the position of $X_6$ is N have a tendency to cyclize. Such peptides, wherein $X_6$ is N, and synthetic proteins of the invention including them, are preferably used within about 10 days, and most preferably within 3 days, after the peptides are synthesized. When employed directly, without conjugation to carrier protein, to immunize B cells in vivo (e.g., Example VII) or in vitro (e.g., the Boss procedure described below), preparatory to making hybridomas, these peptides wherein $X_6$ is N are preferably used within 12 hours after synthesis (i.e., after deprotection of side chains of the peptide).

The synthetic proteins of the invention are made by conjugating a synthetic peptide of the invention with a suitable immunogenic carrier protein using standard techniques with a bifunctional conjugating agent such as carbodiimide, glutaraldehyde or bis-diazotized benzidine.

As indicated supra, it is preferred that the synthetic peptide of the invention include a single tyrosine residue at its amino- or carboxy-terminus and that the conjugation between synthetic peptide and carrier protein occur by reacting the synthetic peptide with the carrier protein in the presence of BDB. This conjugation reaction can be carried out by a known procedure (Bassiri et al., in Methods of Radioimmunoassay, Jaffe and Behrman, eds., Academic Press, New York, N.Y. (1979), pp. 45–47).

The result of this conjugation reaction will be a mixture of synthetic proteins of the invention, each involving a different number of molecules of synthetic peptide conjugated per molecule of carrier protein. The synthetic proteins can be separated from the peptides and BDB of the conjugation-reaction mixture by dialysis. The synthetic proteins of the invention can be, and preferably are, used as a mixture of different proteins, each with a different number of synthetic peptides attached.

If desired, the synthetic proteins can be separated according to the number of attached synthetic peptide molecules; and each type of synthetic protein can be used separately. Separation of synthetic proteins of the invention according to the number of synthetic peptide molecules attached can be carried out by standard techniques for protein purification, such as various chromatographic techniques, including high performance liquid chromatography.

Following the conjugation procedure (see Example III) with BSA and the synthetic peptide with the sequence SCDIFTTSRGKRASKGY, it is found that, on the average, 20 molecules of synthetic peptide are conjugated to each molecule of BSA. When KLH is used in place of BSA, it is found that, on the average, 200 molecules of the synthetic peptide are conjugated to each molecule of KLH.

The synthetic peptides and synthetic proteins of the invention are capable of raising in a mammal an immune response against rabies virus.

A necessary concomitant of an immune response against rabies virus in a mammal is the presence of anti-rabies antibodies in the mammal's serum and the presence of anti-rabies antibody-secreting plasma cells (B cells) in its spleen, lymph, blood and other tissues associated with its immune system.

These anti-rabies antibodies, raised by inoculation of a mammal with a synthetic peptide or synthetic protein of the invention, will bind rabies virus or rabies virus coat protein at one or more antigenic determinants involved in binding of the virus (or coat protein) to the AChR at the ACh binding site. This is because the synthetic peptides of the invention, with which the mammal was inoculated directly or as part of a synthetic protein, has a sequence which comprises a sequence which is the same as that of such an antigenic determinant or differs from such antigenic-determinant sequence by a number of neutral amino acid substitutions which do not prevent the synthetic peptide, free or conjugated to carrier protein, from adopting a set of conformations substantially similar to at least a subset of the conformations of the antigenic determinant on the coat protein embedded in viral coat.

Thus, a mammal inoculated with a synthetic peptide or a synthetic protein of the invention, so that an immune response against the synthetic peptide (free or as part of a synthetic protein) is raised in the mammal, will produce anti-rabies antisera which includes antibodies which will inhibit the binding of rabies virus (or rabies virus coat protein) to cells which are susceptible to such binding by virtue of having AChR receptors on their surfaces. This inhibition is due to competition, between the binding site on the antibodies and the ACh binding-site on the AChR, in binding the segment of the rabies virus coat protein which, in the course of rabies virus pathogenesis, normally binds to the ACh binding site at the AChR, at mammalian neuromuscular junctions. Lentz et al., Science 215, 182–184 (1982) describe assay systems whereby ability of an antibody or mixture of antibodies to inhibit the binding of rabies virus or rabies virus coat protein to AChR-possessing cells susceptible to such binding can be determined.

An alternative test for determining whether a synthetic peptide or protein is capable of raising in a mammal an immune response against rabies virus is to produce antisera in a mammal using the synthetic peptide (conjugated to a suitable immunogenic carrier protein) or synthetic protein as immunogen and then test the antiserum (or the immunoglobulin fraction therof) for the ability to bind to or neutralize rabies virus or rabies virus glycoprotein in any standard binding or neutralization assay known in the immunological arts. For example, the antiserum (or immunoglobulin fraction) can be assayed in an enzyme-linked immunosorbent assay (ELISA) for the presence of antibody against rabies virus coat glycoprotein or inactivated rabies virus.

Yet another means for determining whether a synthetic peptide or synthetic protein is capable of raising an anti-rabies immune response in a mammal is to test the synthetic peptide (conjugated to a suitable immunogenic carrier protein) or synthetic protein on a group of mammals that are not immune to rabies virus to determine whether the peptide or protein is capable of conferring on the mammals protection against challenge by live rabies virus. The group of test mammals is randomly divided into two subgroups, which statistically are substantially the same. All of the animals in one of the subgroups are inoculated with the synthetic peptide (conjugated to a suitable immunogenic carrier protein) or synthetic protein being tested (hereafter referred to as "test peptide or protein") and all of the animals of the other group are inoculated by the same route with a composition that is the same as that of the composition used on the first group except that it lacks the test peptide or protein. If a synthetic protein is tested, the second group might receive carrier protein not conjugated with synthetic peptide. Otherwise, both groups are treated substantially the same. After all of the animals in both groups are inoculated according to a protocol which would be expected to give rise to an anti-rabies immune response, if the test peptide or protein is effective in raising such a response, they are challenged with a dose of live rabies virus which; within a known period of time after challenge (the "$LD_{50}$ period"), would be expected to be lethal to at least 50% of the test mammals that have not mounted an immune response against the virus. If, after the $LD_{50}$ period, significantly fewer of the subgroup which received the test peptide or protein than of the other subgroup have died, the test peptide or protein is capable of raising an anti-rabies immune response in a mammal. A test exemplifying this procedure is described in Example VI.

A composition for vaccinating mammals against rabies is prepared with a synthetic protein of the invention by combining said protein with adjuvants, such as complete or incomplete Freund's adjuvant, aluminum oxide, alum and the like, and diluents, such as PBS. Adjuvants and diluents employed are physiologically acceptable for the mammal to be vaccinated. Such a vaccine can contain more than one species of synthetic protein of the invention. For example, as noted supra, in preparing a synthetic protein of the invention, a range of molecules of synthetic peptide will be conjugated to molecules of carrier protein. It is not necessary to separate these variably conjugated species for preparing the vaccine. Also, synthetic proteins in a vaccine of the invention may carry different synthetic peptides of the invention, although it is preferred that a single species of synthetic peptide be employed in any particular vaccine preparation of the invention.

Methods of preparing anti-rabies vaccines of the invention, using synthetic proteins of the invention as the essential ingredient, are well known in the veterinary and human vaccine arts.

The anti-rabies vaccines of the invention may be employed in three ways. First, they can be used prophylactically, to immunize a mammal prior to its exposure to rabies virus to reduce the risk that, if it should be exposed, it will develop rabies. Second, the vaccines can be used therapeutically, to prevent rabies in a mammal once it has been exposed to live virus. Third, the vaccines of the invention may be used to prepare in a mammal, for use outside the mammal, anti-rabies antisera, associated anti-rabies antibodies, and anti-rabies antibody-secreting B cells.

In all of these applications, the vaccine is preferably administered by intramuscular injection.

When used prophylactically, the vaccine of the invention will typically be administered at least twice to a mammal to be treated, the second dose being typically about a week to 10 days after the first. Preferably a third dose, three weeks to two months after the second, will also be given. Booster doses will typically be administered, if at all, at least six months apart starting at least six months after the initial series of immunizations. Booster doses will be given only if there is reason to believe that anti-rabies antibody titer in a mammal's serum has become too low to be protective in view of the risks of exposure to rabies virus faced by the mammal. Each dose, the initial doses and booster dose, will contain an amount of synthetic protein between about 0.001 milligrams and 100 milligrams depending on the species, age, weight, medical condition, and serum anti-rabies antibody titer of the mammal being vaccinated, the molecular weight of the immunogenic carrier protein portion of the synthetic protein which is the active ingredient of the vaccine and the average number of molecules of synthetic peptide conjugated to each molecule of the carrier protein. The volume of a dose of vaccine is between about 0.01 milliliter and 10 milliliters, depending on the species and size of the mammal being vaccinated, the amount of synthetic protein to be delivered in the dose, and the concentration of said protein in the vaccine preparation.

When used therapeutically, the vaccines of the invention will be used in a manner which generates a high titer of anti-rabies antibody in the serum of the vaccinated animal more quickly than when the vaccine is used prophylactically. A mammal that has been exposed to rabies virus is vaccinated therapeutically following a protocol which is the same for mammals that were not prophylactically vaccinated as for those that were. This therapeutic vaccination protocol involves three to ten doses beginning as soon as possible after the exposure. A second dose will be administered within about two to five days after the first, and a third within about three to six days after the second. A fourth and fifth doses at about twelve to eighteen days and 25 to 30 days after the first, and subsequent doses, up to about five additional, at about monthly or bimonthly intervals after the fifth, may be given. As understood by the skilled in the veterinary and human vaccine arts, dosage strength and volume for therapeutic vaccinations will depend on the same factors as for prophylactic vaccinations.

Although it is generally inadvisable to delay initiating therapeutic vaccination if there is any reason to believe a mammal has been exposed to rabies virus, it is desirable to avoid administering vaccine if it is not necessary to do so. Thus, preferably, in the course of subjecting a mammal to therapeutic vaccination, its tissue or body fluid from the site of suspected contact with rabies virus and tissue or saliva from the animal which is the suspected source of the virus, if the suspected source is an animal, will be assayed for the presence of rabies virus. Further, if a mammal has been exposed to live virus and does consequently undergo therapeutic vaccination, the mammal's serum can be assayed periodically for anti-rabies antibody titer. If the titer becomes sufficiently high, it might be unnecessary to administer one or more doses in the therapeutic vaccination protocol. See ACIP (July 20, 1984), supra.

The vaccines of the invention can also be employed, prophylactically or therapeutically, together with anti-rabies vaccines in which the active ingredient is inactivated or attenuated rabies virus. As has been reported for synthetic-peptide-based vaccines against other viruses, the vaccines of the invention can be employed to prime a vaccinee's immune system to rapidly mount a significant immune response upon exposure to live rabies virus or vaccination with whole, inactivated or attenuated rabies virus. Thus, for example, in a prophylactic vaccination protocol, the first two doses of vaccine may be synthetic-peptide based vaccine of the invention and subsequent doses, including any booster doses, whole rabies virus-based vaccines.

When used to generate in a mammal, for use outside the mammal, anti-rabies antisera or antibodies, or anti-rabies virus antibody-secreting B cells, the vaccines of the invention will also be used to generate quickly a high titer of anti-rabies virus antibody in the mammal. Typically, the mammal will be hyperimmunized with the vaccine. Thus, with mice, typically the vaccine would include complete Freund's rather than a less irritating adjuvant, the animals would be vaccinated about once every other week over a period of two to three months, and the quantity of synthetic protein administered in each dose of the vaccine would be about 25 micrograms to about 200 micrograms, higher than in doses of vaccine needed to protect mice from challenge with live virus. In general, antisera (and associated antibody and B cells) can be raised by following the method of Sigel et al. in Methods of Enzymology, Part E "Immunological Techniques" Vol. 93, pp. 3–12, Academic Press (1983), suitably modified depending on the species of mammal used to produce the sera. For example, if humans are used, use of an adjuvant, such as alum, less irritating than Freund's complete or incomplete, would be indicated and, of course, the quantity of synthetic protein in doses of vaccine would need to be higher than for a smaller mammal.

As noted, supra, anti-rabies antisera of the invention, or anti-rabies antibodies of the invention, from antisera or hybridoma cultures, can be employed therapeutically to confer passive, anti-rabies immunity on a mammal which is susceptible to contracting rabies because it has been exposed to rabies virus. Preferably, to minimize risk of anaphylaxis and other problems associated with infusing proteins from one species into another, antisera or antibody employed in such treatment will be derived from a mammal of the same species as the mammal to be treated. If antibody, polyclonal or monoclonal, is used in the treatment, it will usually be dissolved in a suitable nontoxic diluent such as isotonic saline buffered to about pH7.2 (e.g., PBS) to a concentration of antibody of between about 0.1 and 10 mg/ml. If antiserum is used, it will typically be purified by known methods and used in purified form directly or after concentration to an antibody titer of between about 0.1 and 10 mg/ml. The volume of a dose of antibody preparation is between about 0.1 and 10 microliter per gram body weight of mammal, depending on species, age and medical condition of the mammal and anti-rabies antibody titer of the preparation. A typical dose size with anti-rabies immune globulin with humans is about 130 microliter per kilogram body weight. The volume of a dose of purified, concentrated antiserum is between about 0.1 and 10 microliter per gram body weight of mammal being treated, depending on the same factors considered in determining dose volume with antibody preparation. A typical dose volume with equine anti-rabies antiserum administered to humans is 200 microliters per kilogram body weight. Preferably, for human treatment, an antibody preparation is adjusted, by procedures known in the art based on comparison with a standard reference human rabies immune globulin preparation maintained by the World Health Organization, to an anti-rabies virus antibody titer of 150 international units per ml. Similarly, for human treatment, an antiserum preparation is adjusted, by known procedures in comparison with a reference antiserum preparation maintained by the World Health Organization, to an anti-rabies virus antibody titer of 200 international units per ml.

Preparation and use of the antibody solution (derived from antiserum) or antiserum preparation to treat a mammal that has been exposed to rabies virus follows procedures now employed with anti-rabies immune globulin fraction isolated from plasma of mammals that have been hyperimmunized with inactivated or attenuated rabies virus or anti-rabies antiserum obtained from similarly hyperimmunized mammals. Methods of isolating antibody from hybridoma cultures are well known in the art; such anti-rabies antibodies are used therapeutically in the same way as anti-rabies immune globulin isolated from plasma of mammals hyperimmunized with rabies virus. In general, the method of treatment is to inject about half a dose intramuscularly and, if anatomically feasible, thoroughly infiltrate the other half dose throughout the region of the wound (e.g., bite or scratch) at which virus might have entered. The infiltration is by numerous small-volume injections to the point that swelling occurs around the wound site and even to the point that the pain becomes severe to the mammal being treated. If infiltration at the site at which virus was introduced is not anatomically feasible, the entire dose is administered by intramuscular injection. The treatment with antibody solution or antisera preparation will be as soon as possible after the suspected exposure to rabies virus. A single dose is given.

B cells, preferably splenocytes, from mammals that have been inoculated with anti-rabies vaccines or synthetic peptides of the invention can be employed to make hybridomas which secrete antibodies specific for epitopes with the sequence, or portion of the sequence, of the synthetic peptide which was employed in the vaccine, or employed directly without conjugation to a carrier protein, to inoculate the mammals. Preparation of such hybridoma cultures using such splenocytes follows methods known in the art. See, e.g., Trowbridge, U.S. Pat. No. 4,434,156; Zola and Brooks, in J. Hurell, Monoclonal Antibodies: Techniques and Applications, CRC Press, Boca Raton, Fla. (1982), pp 1–57; Kohler and Milstein, Nature 256, 495–500(1975); and H. E. Schmitz et al., Immunol. Comm. 12, 161–175(1983), all of which are incorporated herein by reference. See also Example VII.

In a typical procedure, splenocytes are taken from the spleen of a mammal that has been hyperimmunized with a vaccine or synthetic peptide of the invention and has mounted an anti-rabies immune response as a result. The splenocytes are then fused to immortalized cells that are compatible with the splenocytes (i.e., capable of forming viable hybrids with the splenocytes) and capable upon fusion with a B cell of expressing and secreting the antibody produced by the B cell, and that possess a selectable marker whereby hybrids with the splenocytes can be selected and identified. After the fusion procedure, cells are cultured in a selective medium, corresponding to the selectable marker of the immortalized antibody-secreting cells, and the cells that survive are subcultured and the subcultures assayed for the production of antibody. The antibody producing subcultures are then further assayed for antibodies which (i) bind to or neutralize rabies virus or rabies virus coat glycoprotein or which inhibit the binding of rabies virus or the rabies virus coat glycoprotein to AChR's on cells which include such receptors, and (ii) bind with a synthetic peptide of the invention (or an analog thereof which lacks a C-terminal or N-terminal Y residue) or a synthetic protein of the invention. Finally, by the technique of limiting dilution, the subcultures which pass the screening test just described are further subcultured to establish clones of single hybrid cells (i.e. single hybridomas), a culture of each of which produces antibody with binding specificity for a single epitope on the segment of the rabies virus coat glycoprotein which is part of, or close to, the segment involved in binding of the protein in the ACh binding-site of the AChR. Such antibodies are capable of inhibiting the binding of rabies virus, or rabies coat glycoprotein, to AChR. The screening of subcultures in the process of limiting dilution is by the same assay techniques used to identify the subcultures from which the limiting dilution is initiated.

Assays for antibody-binding to, or antibody-neutralization of, virus or viral coat glycoprotein and for antibody-inhibition of binding of virus or viral coat glycoprotein to AChR's can be carried out as described above for determinations of whether a synthetic peptide or synthetic protein of the invention has caused an anti-rabies immune response in a mammal inoculated with the synthetic peptide or synthetic protein.

The assays for ability of the antibody or antibodies in a culture (or serum, or other antibody-containing solution, as from a chromatographic purification) to bind to rabies virus, rabies virus coat glycoprotein, synthetic peptide of the invention or synthetic protein of the invention can be carried out by any standard immunoassay technique, such as a radioimmunoassay or an ELISA (enzyme-linked immunosorbent assay) technique. Using a competitive assay between virus (or a viral coat protein) and synthetic peptide (or synthetic protein), the presence of antibody which binds to both virus (or coat protein) and synthetic peptide (or synthetic protein) can be determined.

In assays for antibody-binding to rabies virus, or inhibition by antibody of rabies virus-binding to AChR's, inactivated virus can be employed. Inactivated virus is known in the art and can be obtained from commercially available, whole (inactivated) virus, anti-rabies virus vaccines. For such assays in which rabies virus coat glycoprotein is used in place of whole virus, the glycoprotein can be isolated from whole virus, as known in the art (see Dietzschold et al., supra) or prepared by recombinant DNA techniques as described in Goeddel et al., European Patent Application Publication No. 0 117 657.

In the foregoing procedure for isolating hybridomas cultures, including clones of individual hybridomas, the preferable source of splenocytes is mice, most preferably of the Balb/c or Balb/cByJ strain. Balb/c mice are known and widely available to the art, including from several commercial sources. Balb/cByJ mice are also known in the art and available from Jackson Laboratories, Inc., Bar Harbor, Me., U.S.A. The preferred immortalized antibody-secreting cell lines are those which themselves do not secrete antibody. Two of many examples of such lines known and available in the art are the S194/5.XXO.BUI and the Sp2/0-Ag14 myeloma cell lines, referred to hereinafter as the "S194" and "Sp2" lines, respectively. With hybrids with cells of these two lines, and numerous others, HAT medium, well known in the hybridoma art, is suitable for selection.

The S194 lines is available from, for example, the American Type Culture Collection, Rockville, Md. U.S.A. (ATCC) under ATCC deposit no. CRL 8837. The Sp2 line can also be obtained from, for example, the ATCC, under ATCC no. CRL 1581.

Hybridoma cultures of the invention can also be prepared by a process comprising in vitro immunization of B cells from a mammal (such as splenocytes from a Balb/c or Balb/cByJ mouse) with a synthetic peptide or synthetic protein of the invention. One in vitro immunization procedure, carried out in the presence of a large molar excess (relative to immunogenic protein or peptide of the invention) of an adjuvant peptide such as N-acetylmuramyl-L-alanyl-D-isoglutamine is described in Boss, Brain Research 291, 193–196(1984) and in Boss, U.S. patent application Ser. No. 567,561, filed Jan. 3, 1984, entitled "Hybridoma Production from Cells Immunized in vitro," and assigned to the assignee of the present application; both the paper and patent application are incorporated herein by reference. The preferred immunogens for use in this process of Boss is the peptide SCDIFTTSRGKRASKGY. In this process, after the B cells are immunized in vitro, they are treated in essentially the same way as B cells taken from a mammal after in vivo immunization in preparing hybridoma cultures of the invention.

The hybridoma cultures of the invention, both monoclonal and polyclonal, produce one or more antibodies of the invention. Thus the antibodies produced by these cultures can be employed therapeutically, as described above for antibodies used to treat mammals that have been exposed to rabies virus.

The anti-rabies antibodies described in the present specification, especially the monoclonal antibodies produced by clones of hybridomas, can also be employed diagnostically to determine whether an animal is rabid and to ascertain whether a mammal that is suspected of having been exposed to rabies virus has in fact been so exposed. The antibody, polyclonal or monoclonal, is employed in any of a number of well-known immunoassay techniques to determine whether rabies virus is present in the saliva, salivary glands or brain tissue of an animal being tested for rabies or determine whether rabies virus is present in tissue or fluid from close to the site on an animal's body of suspected exposure to the virus.

The antibody produced by an hybridoma can be generated in very large quantities by a number of techniques known in the hybridoma art. For example, the hybridoma cells can be used to establish an ascites tumor in a suitable strain of mice and antibody secreted by the hybridoma cells of the tumor can be isolated from the resulting ascites fluid.

Because the anti-rabies vaccines of the invention are safer than currently available anti-rabies vaccines, the vaccines of the invention are expected to promote the practice of immunizing mammals, including humans, that are situated so as to be at high risk of exposure to rabies virus. Among the mammals of economic importance for which the vaccines of the present invention are of particular significance are cats, dogs, horses and livestock, including especially bovine and ovine species thereof.

Aspects of the invention will now be illustrated in the following Examples:

EXAMPLE I

Synthesis of Synthetic Peptides With Sequences SCDIFTTSRGKRASKGY and SCDIFTNSRGKRASKGY The title peptides were synthesized manually following the methodology of Merrified. See, e.g., Stewart and Young(1969), supra. Starting resin was a chloromethylated polystyrene resin substituted at 0.54 mmole/gram with BOC-Tyr(4-Br-Z). The BOC-Tyr(4-Br-Z)-substituted resin and the various protected amino acids used in the syntheses were purchased commercially.

The protected amino acids used were as follows:
BOC-Ala
BOC-Arg(Tos)
BOC-Asn(Xan)
BOC-Asp(OBzl)
BOC-Cys(MeOBzl)
BOC-Gly
BOC-Ile(hemihydrate)
BOC-Lys(Z)(dicyclohexylamine salt)
BOC-Phe
BOC-Ser(Bzl)
BOC-Thr(Bzl)
BOC-Tyr(4-Br-Z)

Each addition was carried out as follows:
1. Wash once for 15 minutes with 50% (v/v) trifluoroacetic acid in methylene chloride. Drain.
2. Wash six times, 1 minute each, with methylene chloride, and drain after each.
3. Wash twice, 1 minute each, with 10% (v/v) diisopropylethylamine in methylene chloride, and drain after each.
4. Wash six times, 1 minute each, with methylene chloride and drain after each.
5. Add 4 equivalents of protected amino acid (relative to the amount of resin-bound Tyr prior to start of the synthesis) and agitate for 5 minutes.
6. Add 4 equivalents of DCC (molar amount equal to that of protected amino acid added) and agitate for 1 hour.
7. Add DMF and agitate for 30 minutes, then drain.
8. Wash six times, 1 minute each, with methylene chloride, and drain after each.
9. Carry out ninhydrin test for reaction completeness.

In the synthesis of SCDIFTTSRGKRASKGY, double couplings were required for I, T at position 7 and R at position 9. Acetic anhydride capping was performed after the second coupling of T at position 7.

In the synthesis of SCDIFTNSRGKRASKGY, double couplings were required for I and R at position 9.

The completed peptides were cleaved from the resin and deprotected with anhydrous hydrogen fluoride and then purified by C-18 reverse-phase high performance liquid chromatography.

EXAMPLE II

Radiolabelling of Synthetic Peptides

The peptide SCDIFTTSRGKRASKGY was radiolabeled by iodination of the C-terminal tyrosine by the chloramine T method as follows:

1 millicurie of Na$^{125}$I, in 1.6 to 2.8 microliter of solution made basic (pH 7-11) with NaOH, was added to 10 microliters of 0.5 M sodium phosphate buffer, pH7.4. Then 10 microliters of solution of the peptide, at 0.1 mg/ml, was added. The solution was vortexed for 30 seconds. Then 10 microliters of chloramine T, at 0.1 mg/ml in water, was added and the mixture vortexed for 30 seconds. Then 10 microliters of Na$_2$S$_2$O$_5$, at 0.25 mg/ml, was added and, again, vortexing for 30 seconds was carried out. Then 100 microliters of BSA, at 100 mg/ml in 0.05 M phosphate buffer, was added and the mixture vortexed for 40 seconds. The peptide was separated from non-reacted iodine on a 6 ml Bond-Elut ™ chromatography column (Analytichem International, Harbor City, Calif., U.S.A.) and the radioactive peptide was further purified by high performance liquid chromatography.

EXAMPLE III

Synthetic Proteins

The peptide SCDIFTTSRGKRASKGY was conjugated to BSA with BDB as follows:

BDB solution was prepared by dissolving 5 mg of benzidine dihydrochloride in 1 ml of 0.2 N HCl and adding 3.9 mg NaNO$_2$ in 0.11 ml of distilled water. Reaction was continued for 1 hour at 4° C. with intermittent stirring.

10 mg of BSA, 10 mg of peptide, and 200 microliters of freshly prepared BDB solution were added to 2 ml of a solution 0.16 M in sodium borate (pH 9.0) and 0.13 M in NaCl. Then sufficient 0.5 N NaOH was added to return the pH to 9.0. The mixture was left two hours on ice, then dialyzed overnight at 4° C. against distilled water, and finally dialyzed against 0.15 M NaCl at 4° C. for an additional 24 hours.

The same procedure is followed successfully with 10 mg of peptide SCDIFTNSRGKRASKGY one day after the peptide is synthesized.

The same procedure was followed with 10 mg of KLH in place of the BSA to make the conjugate between KLH and peptide SCDIFTTSRGKRASKGY.

EXAMPLE IV

Anti-Rabies Vaccine Compositions 0.266 ml of the KLH-peptide SCDIFTTSRG-KRASKGY solution (0.15 M NaCl) from Example III was diluted to 5.0 ml in PBS and was then emulsified in 5.0 ml of complete Freund's adjuvant by homogenization at room temperature with an OMNI ™ mixer. The final homogenate contained 200 microgram conjugate per ml. The same procedure was carried out with incomplete in place of complete Freund's adjuvant.

The same procedures are followed with BSA-peptide SCDIFTTSRGKRASKGY conjugate, and BSA-peptide SCDIFTNSRGKRASKGY conjugate.

EXAMPLE V

Production of Anti-Rabies Antiserum in Rabbits

Anti-rabies antiserum is produced in New Zealand male rabbits with the BSA-peptide SCDIFTTSRG-KRASKGY conjugate-based vaccine compositions described in Example IV as follows:

Into each of three of the rabbits, a volume of the vaccine composition containing 150 micrograms of synthetic protein in complete Freund's adjuvant is injected into the exposed retropopliteal lymph nodes of the hind limbs. Two additional intramuscular immunizing doses of the same amount, but emulsified in incomplete rather than complete Freund's adjuvant, are administered at 14 and 28 days after the initial inoculations.

Two weeks after the final dose, antiserum is collected from the ear veins of the rabbits.

The sera are assayed, at each of 1:100, 1:1000 and 1:10000 dilutions, in an immune precipitation assay with the $^{125}$I-labelled synthetic peptide of the synthetic protein of the vaccine composition and polyclonal anti-rabbit IgG antibody preparation, to confirm that each of the sera contains antibodies reactive with the peptide.

EXAMPLE VI

Protection of Mice Against Peripheral Challenge with Rabies Virus

On day 0, two hundred weanling CD-1 mice (Charles River Laboratories), three to four weeks old, 15 to 20 grams, were divided randomly into four groups of 50 each. The 50 mice in one group (Group A) were administered blank compositions, which were the same as the KLH-peptide SCDIFTTSRGKRASKGY conjugate-based vaccine compositions described in Example IV except that KLH alone at 200 microgram/ml, and no synthetic protein or synthetic peptide of the invention, was present in the compositions. The 50 mice in another group (Group B) were administered KLH-peptide SCDIFTTSRGKRASKGY conjugate-based vaccine compositions described in Example IV (200 microgram/ml). The 50 mice in the third group (Group C) were administered at 1:10 dilution of World Health Organization Standard Reference Anti-Rabies Vaccine preparation as obtained from the United States National Institutes of Health. The 50 mice in the fourth group (Group D) were administered neither a blank composition nor any vaccine preparation.

The mice in Groups A and B were each administered blank composition (Group A) or synthetic-protein-based vaccine composition (Group B) by injection according to the following schedule:

| Day | Volume, Adjuvant and Route |
|---|---|
| 0 | 50 microliters, Complete Freund's subcutaneous |
| 21 | 50 microliters, Incomplete Freund's, intraperitoneal |
| 35 | 50 microliters, Incomplete Freund's, intraperitoneal |

On day 49, 25 of the 46 surviving mice in Group A and 25 of the 50 surviving mice of Group B were selected at random and eye-bled to obtain sera for immunoassay. Each eye-bled mouse was returned to the Group from which it had been selected.

Each of the mice in Group C was administered 1:10 dilution of the WHO Standard Reference vaccine preparation by intraperitoneal injection according to the following schedule: 250 microliters on each of days 35, 37, 39, 42, 44, and 46.

On day 49, 25 of the 50 surviving mice of Group D were selected randomly and eye-bled to obtain sera for immunoassay. These eye-bled mice were returned to Group D.

On day 49, each surviving mouse of all four groups was challenged with a 100-microliter, peripheral intramuscular injection of 1:5 fold dilution of a preparation of live Pasteur production seed strain rabies virus provided by Dr. George Baer of the United States Centers for Disease Control, Atlanta, Ga. The mice were observed for 21 days after the peripheral challenge.

The number of challenged mice in each group which died during the 21-day post-challenge observation period, and the mean-time-to death of the mice in each group that died, are indicated in Table VI:

TABLE VI

| Group | Number Challenged | Number Dead | Mean Time to Death (days) |
|---|---|---|---|
| A | 46 | 25 | 10.6 |
| B | 50 | 17 | 11.1 |
| C | 50 | 0 | — |
| D | 50 | 30 | 11.7 |

Each of the 75 serum samples, taken on day 49 from 25 mice each of Groups A, B, and D, were analyzed in a ELISA for antibody against synthetic peptide SCDIFTTSRGKRASKGY as follows:

50 microliters of a solution of peptide at 10 microgram/ml in PBS was incubated overnight (15–18 hours)

at 4° C. in each well of a standard, 96-well polyvinylchloride microtiter plate. After the incubation, the peptide solution was removed from the wells and they were then washed twice with PBS.

To block sites on the surfaces of the wells not occupied by bound peptide, and thereby reduce background due to non-specific binding of antibody from sera being tested and enzyme-linked anti-IgG, 50 microliters of a solution of 5% (v/v) fetal calf serum in PBS or a solution of 10% (v/v) sheep serum, 0.1 M lysine, 0.01% (w/v) NaN$_3$ in PBS (preferably the sheep serum solution) was incubated in the wells for 2 hours at room temperature. After the incubation, the serum solution was removed from each well and the wells were then washed once with PBS.

Next, 50 microliters of a 1:100 dilution in PBS of a serum to be tested was added to each well and incubated in the well at 4° C. overnight.

The wells were then developed using a standard procedure with a conjugate of sheep anti-mouse IgG F(ab')$_2$ with beta-galactosidase and associated indicator system that was obtained from Bethesda Research Laboratories, Inc., Gaithersburg, Md., U.S.A. (Beta-Galactosidase HyBRL-Screen ™ Kit, Catalog No. 95025A) and used according to the manufacturer's instructions.

Of the 25 sera from mice of Group A and the 25 sera from mice of Group D, none was found in the ELISAs to have antibodies to the synthetic peptide.

Of the 25 sera from mice of Group B, 4 were found in the ELISAs to have antibodies to the synthetic peptide.

As indicated in Table VI, administration of the vaccine of the invention provides protection against peripheral challenge with rabies virus. The fraction of animals protected in the protection test described in this Example (approximately 10 of 50 in Group B) correlates well with the number of animals in Group B that raised an immune response against the synthetic peptide (approximately 8 of 50), indicating that protection is related to the generation of antibody against synthetic peptide of the invention.

EXAMPLE VII

Hybridomas Secreting Anti-Rabies Antibody

A composition for inoculation of a mammal with synthetic peptide SCDIFTTSRGKRASKGY was prepared by emulsifying 2 mg of the peptide (dissolved in 1 ml of PBS) in 1 ml of complete Freund's adjuvant by homogenization at room temperature with an OMNI ™ mixer.

Following the procedure of Schmitz et al., supra, 7 adult Balb/cByJ mice, of approximately 20 grams, purchased from Jackson Laboratories, Inc., Bar Harbor, Me., U.S.A., were each administered, by intradermal injection at the base of the tail, on day 0, 100 microliters of the solution of peptide in complete Freud's (100 micrograms of peptide). On day 7, the 5 surviving mice were eye-bled and their sera assayed in an ELISA for antibody against the peptide, as described in Example VI. None of the 5 sera samples showed significant titer of such antibody. On day 14, the 5 mice were again administered, by intradermal injection at the base of the tail, 100 microliters of the composition of peptide in complete Freund's (100 microgram peptide). On day 21, all 5 were again eye-bled and their sera assayed in the ELISA for anti-peptide antibody. All five sera showed a high titer of such antibody.

On day 32, one of the 5 mice was administered, by intraperitoneal injection, 100 microliters of a solution of 1 mg of the peptide in 2 ml of PBS (50 microgram peptide).

On day 36, the spleen was taken from the mouse; and fusion of the splenocytes with cells of the Sp2 line was carried out using standard procedures. Cultures of viable hybrid cells are identified by growth in HAT medium.

Cultures are initially screened for the presence of antibody against synthetic peptide by an ELISA of culture supernatants, carried out essentially like the ELISA described in Example VI. Cultures passing the initial screen are then screened in an ELISA, also essentially according to that of Example VI, for antibody which binds to inactivated rabies virus obtained from anti-rabies vaccine purchased from Wyeth Laboratories, Philadelphia, Pa., U.S.A. under the trademark, WYVAC ®.

By the process of limiting dilution, employing the two assays of the previous paragraph and starting from cultures which pass the screen for anti-virus antibody, monoclonal hybridoma cultures which produce antibody that binds to both the peptide and the inactivated rabies virus are obtained.

While the invention, and how to make and use it, have been described in some detail in the specification and examples, it will be clear to one with ordinary skill in the pertinent arts that numerous modifications can be made without departing from the spirit and scope of the invention. Such modifications are intended to be within the invention described and claimed herein.

What is claimed is:

1. A composition for vaccinating a mammal against rabies which comprises a synthetic protein, which comprises (i) a peptide which has an amino acid sequence comprising the sequence

CDIFTX$_6$SRG, wherein X$_6$ is N or T, conjugated to (ii) a carrier protein which is immunogenic in a mammal, said synthetic protein being capable of raising in said mammal an immune response against rabies virus.

2. A composition according to claim 1 wherein the peptide conjugated to the carrier protein has an amino acid sequence of Y$_i$X$_{-1}$CDIFTX$_6$SRGKRASX$_{14}$G(Y)$_j$, wherein one of i and j is 0 and the other is 1 and wherein X$_{-1}$ is S or P, X$_6$ is N or T and X$_{14}$ is N or K.

3. A composition according to claim 2 wherein the peptide conjugated to the carrier protein has the amino acid sequence

SCDIFTTSRGKRASKGY.

4. A composition according to claim 2 wherein the carrier protein is BSA or KLH and wherein the peptide and carrier protein are conjugated with BDB.

5. A composition according to claim 3 wherein the carrier protein is BSA or KLH and wherein the peptide and carrier protein are conjugated with BDB.

6. An anti-rabies antiserum made by a method which comprises injecting a mammal with an immunogenic amount of a synthetic protein which comprises (i) a peptide, which has an amino acid sequence comprising the sequence

CDIFTX$_6$SRG, wherein $X_6$ is N or T, conjugated to (ii) a carrier protein which is immunogenic in the mammal.

7. An antiserum according to claim 6 wherein, in the method of making the antiserum, the peptide conjugated to the carrier protein has an amino acid sequence of $(Y)_i X_{-1} CDIFTX_6 SRGKRAX_{14} G(Y)_j,$ wherein one of i and j is 0 and the other is 1 and wherein $X_{-1}$ is S or P, $X_6$ is N or T, and $X_{14}$ is N or K.

8. . An antiserum according to claim 7 wherein, in the method of making the antiserum, the peptide conjugated to the carrier protein has the amino acid sequence

SCDIFTTSRGKRASKGY

9. An antiserum according to claim 7 wherein, in the method of making the antiserum, the carrier protein is BSA or KLH and the peptide and carrier protein are conjugated with BDB.

10. An antiserum according to claim 8 wherein, in the method of making the antiserum, the carrier protein is BSA or KLH and the peptide and carrier protein are conjugated with BDB.

11. An antiserum according to claim 9 wherein, in the method of making the antiserum, the injected mammal is a mouse, rat, rabbit, horse, or human, and the mammal is hyperimmunized with the synthetic protein.

12. An antiserum according to claim 10 wherein, in the method of making the antiserum, the injected mammal is a mouse, rat, rabbit, horse, or human, and the mammal is hyperimmunized with the synthetic protein.

* * * * *

UNITED STATES PATENT AND TRADEMARK OFFICE
CERTIFICATE OF CORRECTION

PATENT NO. : 4,707,356
DATED : November 17, 1987
INVENTOR(S) : James W. Patrick et al.

It is certified that error appears in the above-identified patent and that said Letters Patent is hereby corrected as shown below:

| | |
|---|---|
| Column 4, Line 66: | In the first sequence, between "P" and "L" insert an --R--. |
| Column 5, Line 6: | Change "B:" to --B.--. |
| Column 8, Line 40: | Change "$A_{14}$" to --$X_{14}$--. |
| Column 8, Line 51: | Change "$A_6$" to --$X_6$--. |
| Column 8, Line 51: | Change "$A_{14}$" to --$X_{14}$--. |
| Column 15, Line 51: | Change "Enzymobeads TM" to --Enzymobeads $^{TM}$--. |
| Column 15, Line 61: | Change "$X_{31\ 1}C$" to --$X_{-1}C$--. |
| Column 24, Line 58: | Change "Bond-Elut TM" to --Bond-Elut $^{TM}$--. |
| Column 25, Line 27: | Change "OMNI TM" to --OMNI $^{TM}$--. |
| Column 28, Line 17: | Change "WYVAC®" to --WYVAC$^{®}$--. |

Signed and Sealed this

Fourteenth Day of June, 1988

Attest:

DONALD J. QUIGG

Attesting Officer     Commissioner of Patents and Trademarks